United States Patent [19]

Nicholson

[11] Patent Number: 5,061,183

[45] Date of Patent: Oct. 29, 1991

[54] ACID ETCH FOR BONDING CERAMIC ORTHODONTIC BRACKETS

[76] Inventor: James A. Nicholson, 3007 S. Haven, Hattiesburg, Miss. 39401

[21] Appl. No.: 434,291

[22] Filed: Nov. 13, 1989

[51] Int. Cl.$^5$ .............................................. A61C 5/00
[52] U.S. Cl. ................................................. 433/228.1
[58] Field of Search ...................................... 433/228.1

[56] References Cited

PUBLICATIONS

Caries Res.: 2–26 (1974), Journal of the European Organization for Caries Research, vol. 8, No. 1, 1974, "Fissure Sealants. Laboratory Studies" by Silverstone Note, pp. 6–9.

Primary Examiner—V. Millin
Attorney, Agent, or Firm—Dowell & Dowell

[57] ABSTRACT

A solution or gel for use in etching the surface of teeth in preparation for the bonding of ceramic orthodontic brackets and which contains phosphoric acid in an amount not be exceed approximately 5% by weight of the solution or gel compound.

11 Claims, No Drawings

ACID ETCH FOR BONDING CERAMIC ORTHODONTIC BRACKETS

BACKGROUND OF THE INVENTION

1. Field of the Invention

This invention is generally directed to acid etch solutions which are used in preparing the surface of teeth prior to the bonding of orthodontic brackets thereto and more specifically to either a solution or gel etch which contains minor amounts of phosphoric acid. The amount of phosphoric acid in the etch should not exceed approximately 5% by weight of the solution or gel compound and preferably should be within a range of approximately 0.51 to 1.02%. The acid etch of the present invention is specifically designed to prepare the tooth surface for the application of ceramic orthodontic brackets. The solution is specifically formulated to permit sufficient etching of a tooth surface so as to insure a strong and secure bond of the ceramic bracket to the tooth surface but which allows the bracket to be easily removed by the orthodontist without causing hard to the exterior enamel of the tooth and without the need to grind or use excessive force to remove the bracket from the tooth surface.

In other embodiments of the invention, the exact percent of phosphoric acid in solution or in the gel compound may vary slightly depending upon the configuration of the base of the ceramic bracket. It is invisioned that the bases of some ceramic brackets may be ribbed or otherwise configured so that the entire base of the bracket does not contact the tooth surfaces. In these instances, the percentage of phosphoric acid may be increased due to the decrease in surface area of the base portion of the bracket in contact with the tooth surface.

2. History of the Related Art

In preparing teeth for the application of orthodontic brackets, it is first necessary that the surface of the teeth be cleaned and then etched. Cleaning is accomplished by using a prophy brush with a flour-of-pumis and water solution after which the surface of the tooth is thoroughly rinsed and dried utilizing compressed air. Thereafter, the surface to which an orthodontic bracket is to be secured is etched with an acidic etching solution with the application of the etching solution being made utilizing small cotton processor pellets. The etching solution is applied for approximately 60 seconds after which the etching solution is rinsed thoroughly with water and the surface of the tooth again dried. The acid etch is applied to the tooth in order to slightly roughen the exterior surface enamel so as to promote an effective bonding of an after applied bonding agent or agents which will be utilized to secure the orthodontic bracket to the surface of the tooth.

In conventional acid etch solutions which incorporate phosphoric acid, the amount of phosphoric acid is normally present in a range between approximately 37 to 50% by weight in solution or in a gel compound. The use of such conventional phosphoric acid etches has proved to be reliable when applying metallic and plastic brackets. However, with the advent of the newer ceramic brackets, a great deal of problems have been encountered by orthodontist and, in particular, with respect to removing the ceramic brackets which have been applied to teeth which have been prepared utilizing conventional phosphoric acid etch solutions. More specifically, the bases of ceramic brackets are usually flat but may exhibit a microscopic or macroscopic honeycomb appearance and the bases may be coated with a silane coupling agent. In practice it has been found that it is often extremely difficult to remove ceramic brackets once they have been applied to the tooth surface. In many instances, surface tooth enamel has been removed concurrently with the removal of ceramic brackets and in some cases tooth fractures have occurred. This has required that, in some cases, ceramic brackets be filed from the surface of the tooth since the brackets cannot be removed by the application of simple pressure utilizing conventional orthodontic tools. The present situation has lead many orthodontist to suspend use of ceramic brackets in many instances.

SUMMARY OF THE INVENTION

This invention is directed to an acid etch which may be either in liquid or gel form and which includes a phosphoric acid which is present in solution in an amount not to exceed 5% by weight. More preferably, the phosphoric acid should be present by weight in the amount between 0.51% and 1.02% with approximately 0.68% to 1.02% being preferred for consistent bond strength and with approximately 0.76 to 0.85% being optimum. The acid etch of the present invention is applied for approximately 15 seconds on permanent teeth utilizing a gentle wiping action with the liquid being applied by a cotton pad or pellet. When in gel form, the gel may be applied to the surface of the tooth for a selected time, such as approximately 15 seconds, after which the gel is removed and the surface of the tooth rinsed with water while the area is aspirated and thereafter the surface dried thoroughly with warm air.

It is a primary object of the present invention to provide a phosphoric or buffered phosphoric acid solution or gel which may be used as an acid etch for preparing the surface of teeth for the application of orthodontic brackets and particularly for ceramic orthodontic brackets and which allows the brackets to be securely bonded to the teeth during treatment but which permits the brackets to be easily removed from the surface of the teeth without destruction to tooth surface enamel and without possibility of tooth fracture.

It is another object of the present invention to provide a phosphoric or buffered phosphoric acid etch solution which may be utilized to prepare the surface of teeth to accept the bonding of a ceramic orthodontic bracket wherein bond strengths of approximately 1,200 PSI can be achieved but wherein the brackets may be easily removed from the surface of the teeth without harm to tooth surfaces by utilizing conventional orthodontic tools.

It is also an object of the present invention to provide an acid etch which utilizes only a minor amount of phosphoric acid in the etch solution or gel compound and which thereby maintains the surface enamel of the tooth in a healthier state by reducing the amount of disruption to the tooth enamel.

DESCRIPTION OF THE PREFERRED EMBODIMENT

As previously discussed, orthodontist have encountered difficulties in removing ceramic orthodontic brackets from teeth after they have been applied. The difficulty with removal results immediately after the brackets have been bonded or cured to the surface of the teeth. In some instances, brackets which are applied with extremely quick curing compounds such as light activated adhesives may be bonded in a matter of seconds. The difficulty in removing ceramic brackets has resulted not only in increased labor on the part of the orthodontist but often results in damage to the surface enamel of patients' teeth or even in teeth being fractured. The removal problems are encountered after initial bonding as well as when brackets have been in use over an extended period of time.

Due to the problem of removing ceramic brackets, many orthodontist have turned away from the use of such brackets in orthodontic procedures. It is, however, now been determined, that ceramic brackets may safely be applied and secured to teeth and may be bonded with sufficient bond strength so that the brackets may be utilized in a conventional manner but may be easily removed utilizing conventional dental tools without the application of adverse force to the tooth and without damage to surface tooth enamel or fracturing of patients' teeth.

Through a series of tests and actual applications of ceramic brackets to teeth, it has been determined that the over bonding of ceramic brackets to teeth is not only in part due to the flat configuration of the base of the ceramic brackets but also to the roughness or texture of the etched portion of the surface of the teeth to which the brackets are applied. By way of example, ceramic brackets were applied by first preparing a tooth by cleaning and then etching with a liquid phosphoric acid solution of a type which is conventionally utilized and which contains approximately 43% buffered phosphoric acid in water. As previously mentioned, conventional phosphoric acid etch solutions normally range anywhere between 37% to 50% phosphoric acid by weight. Utilizing the 43% phosphoric acid solution, once the ceramic brackets were bonded to the surface of a tooth, the removal of the bracket was extremely difficult requiring that the bracket be filed in order to prevent possible tooth fracture which could result by placing an extreme amount of force against the surface of the tooth in order to break the bracket away from the tooth.

A series of tests were thereafter made in which the percent of phosphoric acid in solution was reduced with the results of the tests reflected in Table "A".

TABLE "A"

| ACID ETCH DILUTION TESTS | | |
|---|---|---|
| DILUTIONS $H_3PO_4$ TO $H_2O$ | RESULTING PERCENT OF $H_3PO_4$ | RESULT |
| 1-0 | 43.00% | A |
| 1-1 | 21.50% | A |
| 1-2 | 10.80% | A |
| 1-4 | 5.40% | B |
| 1-8 | 2.70% | B |
| 1-16 | 1.35% | B |
| 1-24 | 1.02% | C |
| 1-28 | 0.85% | C |
| 1-30 | 0.76% | C |
| 1-32 | 0.68% | C |
| 1-48 | 0.51% | D |
| 1-64 | 0.34% | E |

A = bond strength too great, possible result of damage to surface enamel or tooth structure.
B = some brackets removable, others only removable with excessive force or requiring filing.
C = brackets easily removed utilizing conventional orthodontic tools.
D = some brackets not sufficiently retained to surface of teeth causing premature displacement of brackets.
E = Numerous brackets not sufficiently retained to surface of teeth With reference to the foregoing table of tests, it is noted that until the dilution resulted in a phosphoric acid concentration of less than 1.35% the ceramic brackets were still difficult to remove from the surface of teeth even though removal was possible in some instances in ranges of acid concentration of approximately 5.40% and lower. Through further testing it has been determined that ceramic brackets may be effectively bonded to the surface of teeth when the teeth are acid etched utilizing etches having a primary active ingredient of phosphoric acid which is present by weight either in solution or in gel for, of between approximately 0.51% and 1.02% however, ranges of between approximately 0.68% to 1.02% are preferred for consistent bond strength. Further, the optimum range appears to be between 0.76% to 0.85%. Within these ranges, the brackets are bonded with an approximate bond strength of 1,200 PSI and therefore are securely bonded for purposes of patient treatment. The brackets, however, are easily removed in the event that re-orientation or replacement or final removal of the brackets following treatment becomes necessary.

Further, it has been determined that if the amount of phosphoric acid in solution is reduced much beyond the 0.51%, that the effective bond of the ceramic bracket with respect to a tooth surface is often not sufficient to permit patient treatment as numerous bonds are too weak to retain the brackets during normal use.

Although the tests also indicate that some brackets may be removed when the phosphoric acid is diluted to approximately 5.0% or less, in many instances, the bond remained sufficiently strong to create a potential hazard of destruction to tooth enamel caused by the physical removal or filing of the brackets from teeth. It is expected, however, that the use of phosphoric acid solutions within the 5.0% to 1.0% range would be possible if the base of the ceramic brackets were varied so that the bases surface did not continuously contact the surface of teeth when applied. Therefore, if the contact surface of the base of a ceramic bracket is dimpled or ribbed or otherwise constructed so that only portions of the base engage the surface of a tooth, then effective bonds can be created by etching the surface of teeth utilizing a phosphoric acid etch solution or gel having phosphoric acid present between approximately 1.0% to 5.0%. However, when using ceramic brackets that have a continuous contact surface on the base portion, the tests indicate that phosphoric acid should only be present in the solution between approximately 0.51% to approximately 1.02% as discussed above.

The phosphoric acid solutions utilized in performing the tests disclosed in Table "A" utilized a buffered phosphoric acid in water. It is envisioned that the etching solutions may include other non-active etching ingredients other than phosphoric acid and yet still fall within the teachings of the present invention which indicate an optimum range for the amount of phosphoric acid by weight which can be in solution to perform surface etching of teeth in preparation for ceramic bracket bonding.

In addition to the foregoing, the test were conducted in such a manner that the acid etch solutions were applied to the surface of teeth by utilizing cotton pads or pellets which are gently wiped across the surface of the tooth in the area to which the bracket is to be bonded for a period of approximately 15 seconds for permanent teeth and for approximately 30 to 60 seconds on deciduous teeth or permanent teeth with Flourosis. At all times during the application of the etching solution, a visible layer of the solution should be present and the solution should not be allowed to dry on the surface of a tooth.

Once the surface of the tooth has been treated with the acid etch solution or a gel the tooth is rinsed with water while the area is aspirated and thereafter the area is thoroughly dried with warm air.

As with conventional phosphoric acid etches, care should be taken to avoid skin contact or contact with oral mucosa, eyes and dentin so as to prevent possible injury to the patient.

Although the phosphoric acid may he utilized in aqueous solutions which may include other agents which are not active in the etching of the surface of tooth, the solutions may be created in gel form by adding thickners to the phosphoric acid solution to increase the viscosity of the solutions. In this manner gel-like products may be obtained which may be applied to the surface of teeth. By way of example, the phosphoric acid solutions may be blended with hydrophillic silicates, fumed silicates or gelatin which may be present in solution in an amount of approximately 5% or more by weight.

In view of the foregoing, it has now been determined that ceramic brackets may be effectively bonded to the surface of teeth in such a manner that the brackets may be securely retained during treatment but may be easily removed following treatment or to allow for re-alignment of brackets as may become necessary. Further, due to the minor amount of phosphoric acid in solution, it is possible to retain the surface of teeth in a much healthier condition by destroying less of the surface enamel during the etching process and yet still obtain bonds which are sufficient for patient treatment. Through the use of the dilute phosphoric acid etching solutions of the present invention, it will be possible for patients to have the benefit of the ceramic brackets while preventing the possible destruction of surface tooth enamel or tooth fracturing which is presently caused utilizing conventional phosphoric acid etch solutions.

I claim:

1. An acid etch composition for treating the surface of teeth prior to the application of ceramic orthodontic brackets comprising a solution containing phosphoric acid as the active etching ingredient wherein the phosphoric acid is present in solution in an amount not to exceed approximately 5% by weight, and said composition containing sufficient fillers to form a gel.

2. The etch composition of claim 1, wherein the phosphoric acid is present in an amount between approximately 0.51% to 1.02%.

3. The etch composition of claim 1, wherein the phosphoric acid is present between approximately 0.76% to 0.85%.

4. A method of etching the surface of teeth in preparation for the bonding of orthodontic brackets comprising the steps of; applying to the surface of the teeth an acid etch solution having phosphoric acid present in solution between approximately 0.51% to 1.02% by weight for periods of between 30 and 60 seconds, thereafter rinsing the surface of the tooth and drying the surface of the tooth with air.

5. A method of etching the surface of teeth in preparation for the bonding of orthodontic brackets comprising the steps of; applying to the surface of the teeth an acid etch solution having phosphoric acid present in solution between approximately 0.51% to 1.02% by weight for periods of approximately 15 seconds, thereafter rinsing the surface of the tooth and drying the surface of the tooth with air.

6. An acid etch composition for treating the surface of teeth prior to the application of orthodontic brackets comprising phosphoric acid as the active etching ingredients wherein the phosphoric acid is present in an amount not to exceed approximately 5% by weight, said composition containing sufficient fillers to form a gel.

7. The etch composition of claim 6, wherein the phosphoric acid is present in an amount between approximately 0.51% to 1.02%.

8. The etching composition of claim 6, wherein the phosphoric acid is present between approximately 0.76% to 0.85%.

9. A method of etching the surface of teeth in preparation for the bonding of orthodontic brackets comprising applying to the surface of the teeth an acid etch having phosphoric acid present in an amount not to exceed approximately 5.0% by weight and thereafter rinsing the surface of the tooth.

10. The method of claim 9 in which said acid etch is applied for a period of up to 60 seconds.

11. The method of claim 9 in which said acid etch includes a solution of phosphoric acid present in an amount between 0.51% to 1.02% by weight.

* * * * *